United States Patent [19]

Davis et al.

[11] Patent Number: 5,328,451
[45] Date of Patent: Jul. 12, 1994

[54] IONTOPHORETIC DEVICE AND METHOD FOR KILLING BACTERIA AND OTHER MICROBES

[75] Inventors: Charles P. Davis; Michael M. Warren, both of Galveston, Tex.

[73] Assignee: Board of Regents, the University of Texas System, Austin, Tex.

[21] Appl. No.: 745,592

[22] Filed: Aug. 15, 1991

[51] Int. Cl.⁵ .............................................. A61N 1/30
[52] U.S. Cl. ...................................... 604/20; 604/21; 422/22
[58] Field of Search .................... 604/20, 21; 128/362; 422/22; 607/1, 2

[56] References Cited

U.S. PATENT DOCUMENTS

| | | |
|---|---|---|
| 2,121,875 | 8/1933 | Kruse et al. |
| 3,716,054 | 2/1973 | Porter et al. |
| 4,019,510 | 4/1977 | Ellis ........................... 604/20 |
| 4,027,393 | 6/1977 | Ellis et al. .................. 604/20 |
| 4,116,238 | 9/1978 | Pettijohn |
| 4,149,533 | 4/1979 | Ishikawa et al. |
| 4,314,554 | 2/1982 | Greatbatch |
| 4,340,047 | 7/1982 | Tapper et al. |
| 4,406,658 | 9/1983 | Lattin et al. ................ 604/20 |
| 4,411,648 | 10/1983 | Davis et al. ................ 604/21 |
| 4,456,012 | 6/1984 | Lattin |
| 4,569,673 | 2/1986 | Tesi ............................ 604/20 |
| 4,612,100 | 9/1986 | Edeling et al. |
| 4,649,937 | 3/1978 | DeHaan et al. |
| 4,764,164 | 8/1988 | Sasaki |
| 4,786,278 | 11/1988 | Masaki |
| 4,840,182 | 6/1989 | Carlson |
| 4,899,759 | 2/1990 | Pederson et al. |
| 4,966,586 | 10/1990 | Vaillancourt |

FOREIGN PATENT DOCUMENTS

27201776A1 11/1978 Fed. Rep. of Germany.

OTHER PUBLICATIONS

C. P. Davis et al., "Effects of Microamperage, Medium, and Bacterial Concentration on Iontophoretic Killing of Bacteria in Fluid," *Antimicrobial Agents and Chemotherapy*, 1 Apr. 1989, pp. 442–447.
C. P. Davis et al., "Iontophoretic Killing of *Escherichia coli* in Static Fluid and in a Model Catheter System," *Journal of Clinical Microbiology*, May 1982, pp. 891–894.

*Primary Examiner*—Lee S. Cohen
*Attorney, Agent, or Firm*—Arnold, White & Durkee

[57] ABSTRACT

An apparatus and method for killing microbes, including bacteria or yeast-like fungus within or on a conductive medium, is provided including positive and negative electrodes which may be activated to generate antimicrobial agents from within the conductive medium. The agents are any form of anions including atoms or molecules derived from inorganic salts present within the conductive medium. Due to residual killing effect caused by the presence of internally generated antimicrobial agents, constant activation of the electrodes is not necessary thereby allowing intermittent activation in order to prolong the life of the metallic or non-metallic electrodes. Electrode polarity can be reversed periodically to drive precipitation from the electrode surface and to also extend electrode life.

26 Claims, 8 Drawing Sheets

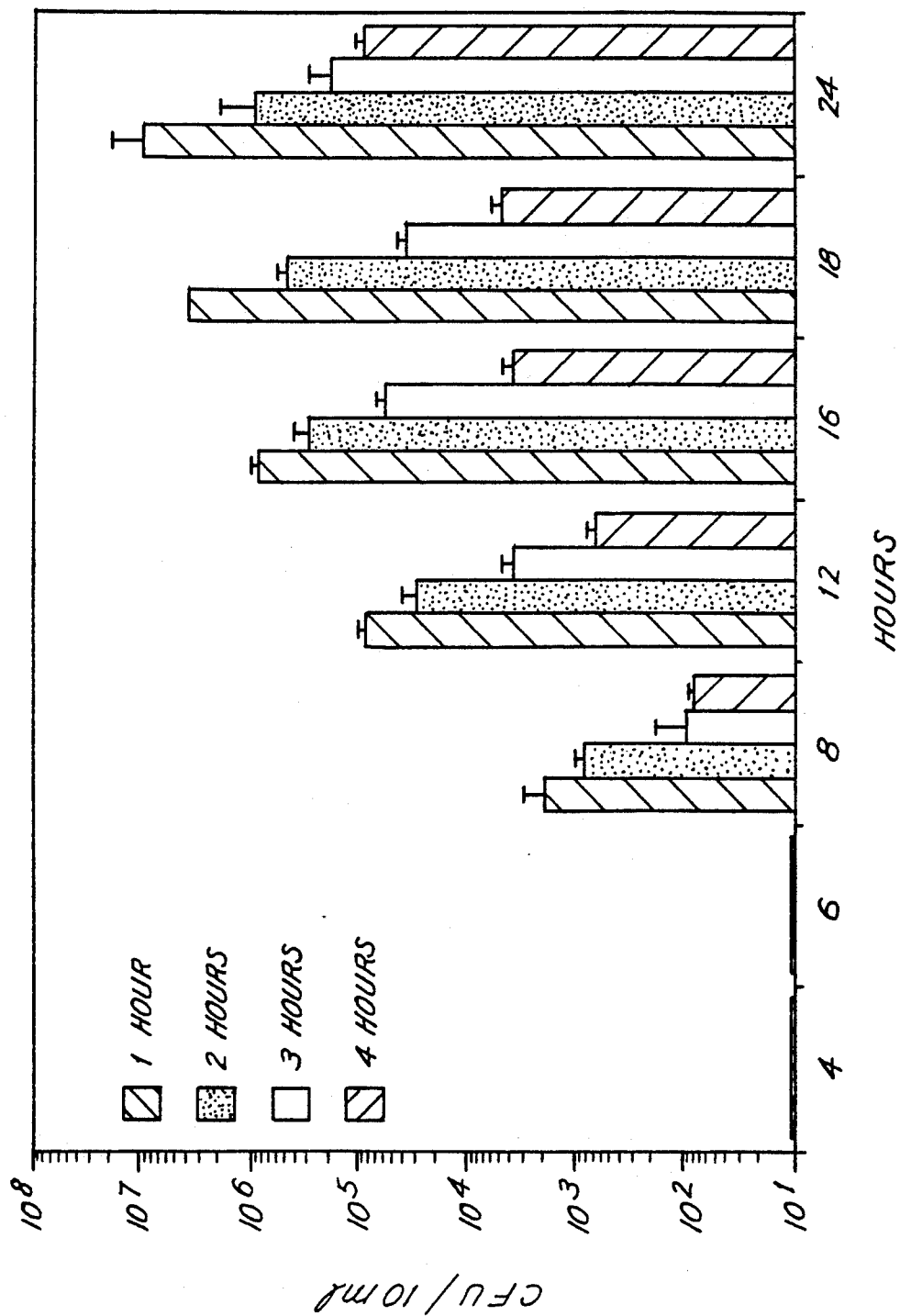

IONTOPHORETIC DEVICE AND METHOD FOR KILLING BACTERIA AND OTHER MICROBES

BACKGROUND OF THE INVENTION

1. Field of the Invention

This invention relates to a device and method for inducing the release of antimicrobial agents from a conductive medium. In particular, the present invention comprises a device and method for the sterilization or reduction of a microbial population in or on a medium by the application of intermittent and/or reverse polarity electrodes placed within or on the medium.

2. Description of the Relevant Art

There are many environments in which it becomes necessary to control the growth of bacteria. During food processing or potable water storage, it is important that the amount of microbes or bacteria be substantially reduced if not eliminated. Equally important is the need for maintaining a sterile environment during most, if not all, surgical operations. Not only must the medical devices which permeates a patient's skin be maintained sterile, but the incision area must also be substantially void of bacteria or microbes.

As a means to reduce or prevent the likelihood of infection following an incision, topical antibiotics are often applied at the point of incision around the medical instrument. In addition, antibiotics can be injected into the physiological system to further ward off infection. Unfortunately, many forms of chemical-based antibiotics may cause serious side effects. Furthermore, if an incision or insertion is maintained over a relatively long period of time such as, for example, when a catheter is place through the skin, detrimental effects caused by long-term antibiotic use is substantially increased.

In an effort to overcome the problems associated with conventional antibiotics, iontophoresis was recently introduced as a means for electrically sterilizing the incision or insertion site. The iontophoresis process consists of introducing a low level current into a conducting medium such as fluid contained within a physiological system. A current is supplied to the electrodes which thereby induces ionic flow of ions from one electrode to the other. Specifically, conventional iontophoretic devices utilize heavy metal ion movement between electrode to produce the desired killing effect. Thus, conventional iontophoresis primarily involves the generation of metallic ions at the electrode surface which are then subsequently driven into the surrounding conducting medium or fluid path by the influence of electromotive force.

Although conventional iontophoresis represents a substantial improvement in long term sterilization, the heavy metal ions generated from the electrode surface likely limits the life expectancy of the electrodes. The out-migration of heavy metal ions from the surface may lead to a reduction in the electrode size and integrity.

Therefore, while conventional iontophoresis devices and methods provide a safer and longer period of sterilization than most forms of antibiotics, their period of use is still limited due to the out-migration process. If conventional iontophoresis is used over extremely long periods such as in a food processing or water treatment environment, then frequent replacement of conventional metallic electrodes is necessary, and would be both time consuming and expensive.

SUMMARY OF THE INVENTION

The problems outlined above are in large part solved by the apparatus and method of the present invention. That is, the present method and apparatus hereof provides a longer term iontophoretic device or method for killing microbes in a conductive medium by inducing and/or utilizing antimicrobial agents from within the conductive medium. The antimicrobial agents of the present invention may come from within the medium rather than entirely from the surface of the electrodes. By utilizing antimicrobial agents and molecules which are nonmetallic, the present invention does not rely solely upon the generation of heavy metal ions to perform iontophoresis. Instead, killing agents of the present invention derives, at least partially, from the medium itself. Thus, the present invention can achieve killing using either metallic or non-metallic electrodes. By activating antimicrobial agents from within the medium rather than entirely from the electrode surface, the present invention can minimize metallic out-migration problems associated with conventional iontophoretic devices. Thus, the present invention can achieve effective long term sterilization without frequent electrode replacement. Infrequent electrode replacement is advantageous when the electrodes are inaccessible or difficult to remove, such as in food processing, water treatment and medical environments, etc.

Still further, the present invention may include an intermittent current source and/or a polarity interchange circuit which acts to pulse low level current within the conducting medium. The pulse or intermittent current helps to increase the life expectancy of the electrodes. In addition, the polarity of the electrodes can be periodically reversed by an electrode polarity interchange circuit of the present invention by reversing electrode polarity thereby driving precipitation accumulation from the electrodes. Polarity reversal of the present invention thereby functions to interchange the role of the anode and cathode so that both electrodes may contribute ions to the medium instead of only one electrode.

By generating antimicrobial agents contained within the medium, and by reverse polarity pulsing the current source, the present invention not only prolongs the life of the electrodes, but also provides long-term residual killing of bacteria, yeasts or other microbes found within or upon the conductive medium. Furthermore, the use of intermittent current may provide a local environment that is more suitable to human tissue. Constant generation of antimicrobial agents may have a deleterious effect on tissue over time. Thus, intermittent generation of antimicrobial agents could feasibly allow human tissue to adjust to the change in the local environment and thus provide better tissue survival. Still further, killing of bacteria, yeast or microbes can be either complete (i.e., sterilization) or merely partial (i.e., reduction in bacteria, yeast or microbial population).

Broadly speaking, the apparatus of the present invention comprises a positive and a negative electrode spaced apart from one another and placeable in a conductive medium. The electrodes can then be activated to generate antimicrobial agents from inorganic salts contained within the conductive medium. Alternatively, antimicrobial molecules or compounds can be generated from within the conductive medium, whereby the molecules preferably include atomic structures of elements such as chlorine. However, other halides such as bromine or fluorine may also exist.

In a preferred embodiment of the present invention, the medium includes a fluid contained within a vessel. In an alternative preferred embodiment, the medium is a conductive region between a biological fluid or gas and a medical tool partially implanted into a patient. In yet another alternative preferred embodiment, the medium is the surface of an open sore or wound, upon which an electrode-contained bandage is placed. In all the preferred embodiments, the fluid or conductive gas contains bacteria, yeast or other microbes from a source such as a water treatment plant or physiological cavity. If the fluid or gas is obtained from a physiological cavity, it can be measured and decontaminated in vitro. Alternatively, the medium can be measured and decontaminated in vivo by inserting a catheter containing the electrodes within the physiological cavity, or placing a bandage or dressing containing the electrodes upon the physiological area.

In one aspect of the present invention, the positive and negative electrodes are made from an element such as gold, silver, platinum, copper, stainless steel and/or carbon. Thus, while metal electrodes may be used, non-metal electrode such as carbon, may also be effectively used.

The positive and negative electrodes can be placed directly into a medium-filled (gas or fluid-filled) container or the electrodes can be placed within a catheter which is then inserted into a vessel (i.e., physiological vessel, etc.). Still further, electrodes can be placed about a medical tool which is partially implanted within a patient. Even still further, electrodes can be placed on the surface of a conductive medium such as an open sore or wound. If the electrodes are placed within a catheter, they are preferably placed about the inside of a catheter or, they may alternatively be placed about the outside of a catheter. If the electrodes are configured inside a catheter, they can provide microbial killing (i.e., sterilization or population reduction) of biological fluids flowing within the catheter. If the electrodes are placed on the outside of a catheter, they can provide microbial killing of fluids flowing along the outside of the catheter as well as at the interface between the catheter and conductive tissue surrounding the catheter. Thus, outside-configured electrodes help prevent microbes from migrating along the outside catheter surface from the outside environment.

In another aspect of the present invention, a current source can provide intermittent current to the positive and negative electrodes. Use of intermittent current upon the electrodes reduces precipitation at the electrode surface while maintaining effective microbial killing over a longer electrode lifespan. An electrode polarity interchange circuit may also be used to prevent the accumulation of precipitation. By reversing the polarity upon the electrodes, ionic exchange is reversed between the electrodes causing reverse accumulation at the electrode site.

The present invention also contemplates a method for sterilizing a conductive medium which includes placing positive and negative electrodes apart from each other and into or on the conductive medium. The positive and negative electrodes are then connected to a current source, and the current source is then activated whereby antimicrobial agents are released from inorganic salt contained within the medium. The positive and negative electrodes can be energized from an intermittent current and/or a reverse polarity current source.

BRIEF DESCRIPTION OF THE DRAWINGS

Other objects and advantages of the invention will become apparent upon reading the following detailed description and upon reference of the accompanying drawings, in which:

FIG. 14 is a graph showing actual results of residual killing of a yeast-like fungus, Candida albicans, from 4 hours to 24 hours after initial sterilization in accordance with the present invention.

Figure 1:
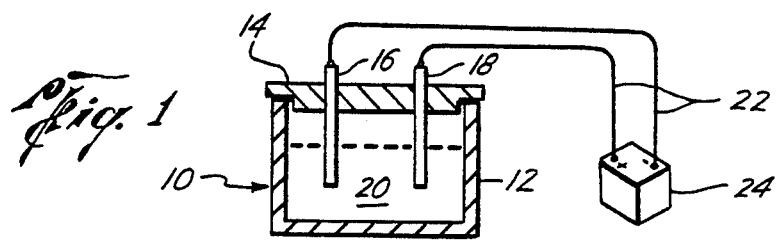
FIG. 1 is an apparatus of the present invention.

While the present invention is susceptible to numerous modifications and forms, specific embodiments thereof have been shown by way of example in the drawings and will herein be described in detail. It should be understood, however, that these specific embodiments are not intended to limit the invention to the particular form disclosed, but on the contrary, the intention is to cover all modifications, equivalents, and alternatives falling within the spirit and scope of the invention as defined by the appended claims.

DESCRIPTION OF THE PREFERRED EMBODIMENTS

Figure 2:
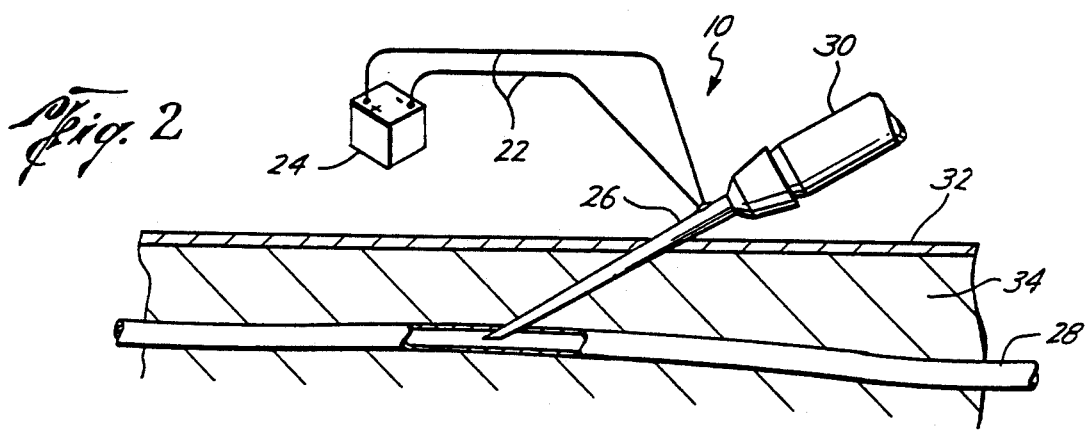
FIG. 2 is another apparatus of the present invention.
Figure 3A:
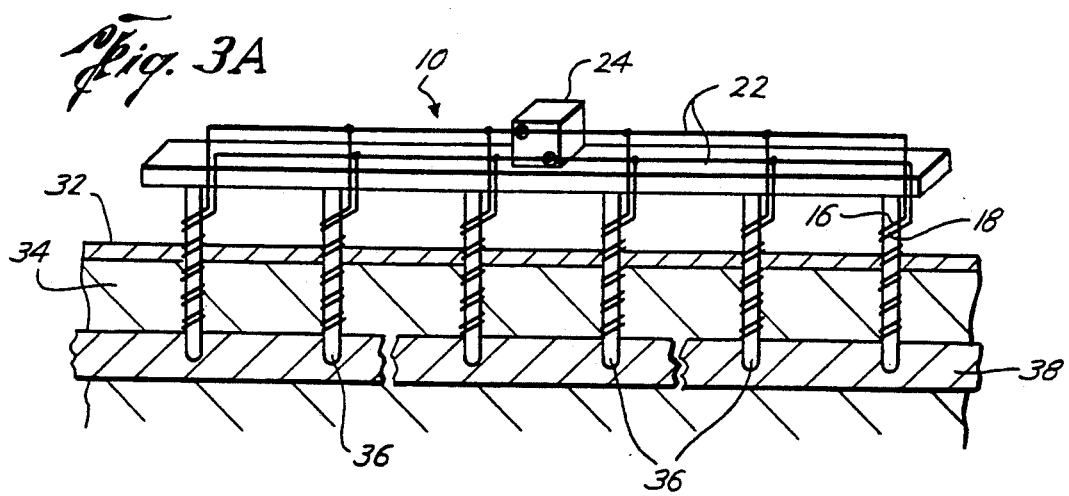
FIG. 3A is still another apparatus of the present invention.
Figure 3B:
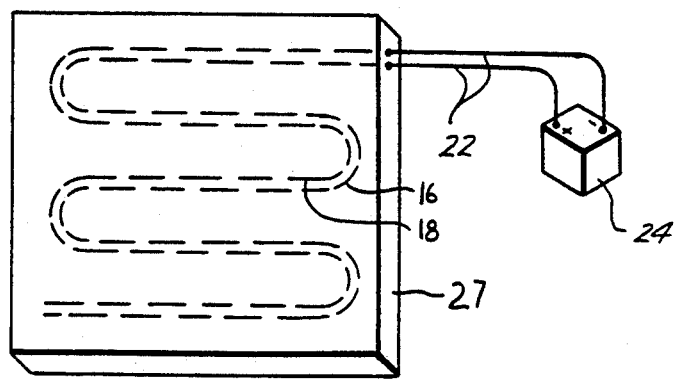
FIG. 3B is yet another apparatus of the present invention.

Turning now to the drawings, FIGS. 1, 2, 3A and 3B illustrate exemplary alternative preferred embodiments of the present invention. FIG. 1 is an iontophoretic device for killing bacteria and/or microbes in bulk medium (i.e., gas or fluids), whereas the catheter of FIG. 2 can be used for killing microbes in vivo within a physiological cavity. Still further, FIG. 3A illustrates iontophoretic killing apparatus used in a conductive medium between a partially implanted medical tool and the surrounding tissue/fluid. Yet further, FIG. 3B illustrates iontophoretic killing apparatus used on the conductive surface area of an open sore or wound. In all the above embodiments, microbial killing occurs causing a reduction or total elimination in the amount of microbes, bacteria or yeast population.

Referring to FIG. 1, an iontophoretic apparatus 10 is shown including a container 12, a lid 14 and a pair of electrodes 16 and 18 secured within lid 14. One end of electrodes 16 and 18 is embedded within a conductive medium 20. There are various forms of conductive medium. Such conductive medium includes fluid, gas, tissue fluid in which live cells exist and/or a matrix connected by fluid filled or gas filled cells. Provided conductive medium 20 contains inorganic salts, possibly containing chloride, and provided the medium is capable of carrying small amounts of current between charged electrodes, any form of medium is suitable for the present invention. Therefore, bulk fluid such as from a water treatment plant or food processing facility may be equally suitable as medium 20 for placement within container 12. The subject fluid can simply be removed from its source and placed in vitro within container 12 upon which subsequent iontophoresis is achieved. Connected to the one end of each electrode 16 and 18 are conductive wires 22. Wires 22 carry current from current source 24 remotely placed from container 12. Source 24 can be any form of power source which can deliver 1–400 $\mu A$ into a fairly high impedance load. Higher current levels may be used in devices not implanted in humans. As will be discussed below, source 24 is capable of delivering intermittent current and/or current at changing polarities.

Referring to FIG. 2, an alternative embodiment for application of the present invention is illustrated. Iontophoretic apparatus 10 comprises a catheter 26 shown having its distal end placed into a cavity or vessel 28 (preferably a physiological vessel). The proximal end of catheter 26 can accommodate any fluid delivery or withdrawal scheme. Preferably, an intravenous tube 30 can be pressure mounted and sealed within the proximal orifice of catheter 26. However, it is to be understood that other forms of fluid delivery or withdrawal tubes can be used such as, a syringe, a pump or heploc chamber. It is also to be appreciated that physiological cavities are those existing in vivo and that the distal end of catheter 26 can be adapted for placement in an artery, vein, bone marrow, intraperitoneal, wound surface or drainage area, internal organs, inner cranial pressure monitoring devices such as Richmond bold assemblies, etc. Conductors are attached at the distal end of wires 22 (see FIGS. 4A–4D). The conductors can be either secured about the outer periphery of catheter 26 or within the catheter. If they are secured to the outer surface, then they function to sterilize at the interface between either (i) skin 32 and catheter 26, (ii) tissue 34 and catheter 26 or (iii) cavity 28 and catheter 26. In either case, killing (i.e., sterilization or microbial population reduction) is achieved to prevent outside contaminates from entering the physiological cavity. Conversely, if the electrodes are placed about the inner surface of catheter 26, they function to kill microbes in the conductive medium or fluid which flows past the electrodes on their journey between cavity 28 and tube 30. Depending upon their placement, electrodes used in a catheter embodiment, such as shown in FIG. 2, represents a substantial improvement over static or in vitro applications of bulk sterilization shown in FIG. 1. At-the-site sterilization provides direct and continuous in vivo sterilization of physiological fluid as the fluid normally exists within the physiological system.

Referring to FIG. 3A, an alternative preferred embodiment is shown for killing microbes at the region surrounding bone stabilization pins 36. In certain orthopedic procedures, a bone 38 requires external stabilization through pins 36 placed periodically into the bone 38 at certain stress points therein. Pins 36 function to hold the bone in position during the healing process. After a period of time, the pins can be quickly and easily removed without undergoing drastic surgical procedures often encountered when completely internal stabilization rods or plates are used. Unfortunately, the pins provide a conduit between a bacteria-laden outside environment and bone 38. It is imperative that contaminants not be allowed to enter the sterile physiological environment (tissue or bone), and accordingly, topical antibiotics are often used at the pin 36 insertion points. Unfortunately, these forms of antibiotics are impractical for long-term sterilization since (i) they may cause unacceptable side effects, (ii) they may be ineffective against certain types or quantities of microbial contamination, and (iii) topical antibiotics generally require periodic application which may be impractical or inconvenient.

In an effort to overcome the shortcomings of topical antibiotics when used with an implanted medical tool such as a stabilization pin 36, FIG. 3A illustrates a portable, low-profile apparatus 10 including pins 36 having electrodes 16 and 18 placed about the outer surface of each pin. The electrodes are connected to a battery operated current source 24 via wires 22. Conductors 16 and 18 are preferably wrapped tightly about the external surface of each pin at the interface between (i) skin 32 and pin 36, and (ii) tissue 34 and pin 36. By applying low current between electrodes 16 and 18, microbes traveling within the interface region are killed before they reach internal tissue 34 or bone 38. Therefore, although microbes may enter the physiological system at the incision points, iontophoretic sterilization of the present invention substantially prevents microbes from remaining or from reaching critical tissue, bone, vascular system, internal organs, etc.

Microbial killing can also occur on the surface of a physiological medium as shown in FIG. 3B. To prevent microbial or yeast formation on the surface of a wound or sore 25, a porous bandage or dressing 27, containing electrodes 16 and 18, is placed upon the wound surface. Activation of the electrodes via current source 24 promotes rapid healing of the wound area while preventing or reducing microbial formation therein.

Turning now to FIGS. 4A–4D, various alternative embodiments are illustrated for placing electrodes 16 and 18 within a catheter 26 environment. Cross-sectional views illustrate various ways in which current path can be established between two corresponding electrodes, the electrodes being on the inside or on the outside of the catheter.

Figure 4A:
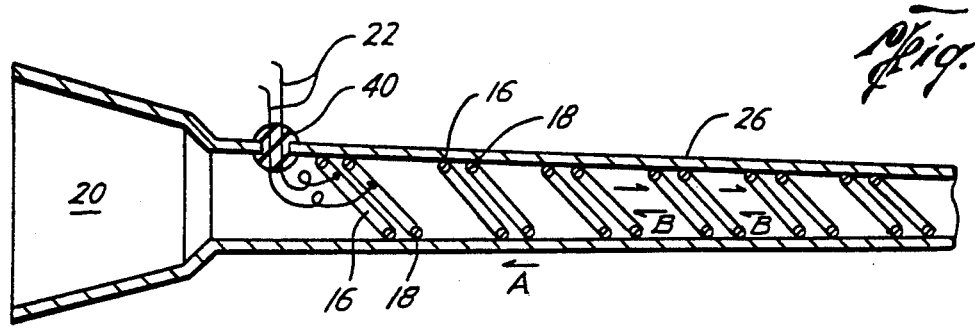
FIGS. 4A–4D are cross-sectional views of various embodiments of a catheter with conductors placed about the inner and outer walls of the catheter in accordance with the present invention.

FIG. 4A illustrates cross-sectional view of a pair of electrodes 16 and 18 placed slightly apart from one another and wound about the inside perimeter of catheter 26. Wires 22 are shown placed through a sealing membrane 40 and are electrically connected to electrodes 16 and 18 wound about the inner diameter of catheter 26. Wires 22 can be connected to remote current source 24. When placed on the internal surface of catheter 26 as shown in FIG. 4A, electrodes 16 and 18 function to kill bacteria or microbes traversing the internal coil made by electrodes 16 and 18.

Generally speaking, and without wishing to be limited to theory of this invention, a current path is established between adjacent electrode pairs 16 and 18. If electrode 18 receives positive polarity from remote source 24, then current will flow as indicated by reference numeral A toward adjacent electrode 16. It is believed that the bactericidal effect of the present invention is a consequence of ionic generation and movement between the electrodes as a result of the current flow. It is furthermore believed that opposite charges upon electrodes 16 and 18 cause the generation of antimicrobial agents from inorganic salts contained within the conductive medium 20 as the conductive medium 20 traverses the coiled electrodes as indicated by flow reference numeral B. Thus "antimicrobial agents" have been used herein as a generic term for a molecule which is generated from inorganic salts found within the conductive medium. These salts preferably have present an atomic structure including chlorine, or possibly fluorine and/or bromine. Antibacterial agents may therefore include anions generated from inorganic salts having at least a chloride ion or chlorine molecule. In view of the physical properties of antimicrobial agents, any element which provides sterilization from inorganic salts found within the conductive medium, fall within the defined meaning of "antimicrobial agents." The use of the term "antimicrobial agents" should not be understood to indicate a specific type of atomic or molecular compound, but defines all possible elements and compounds derived from the medium or the electrode. Specifically, "antimicrobial agents" may include anions selected from the group including chloride.

Figure 4B:
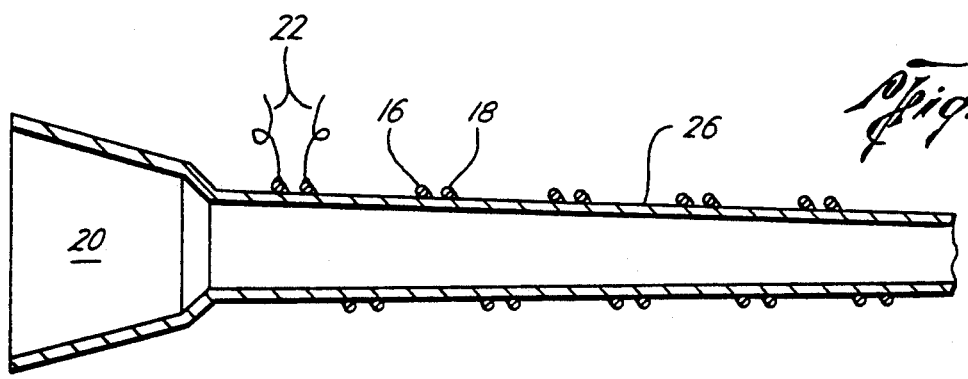

Comparing FIG. 4B to FIG. 4A, FIG. 4B illustrates electrodes 16 and 18 configured as a coil wound about the outer surface of catheter 26. By placing electrodes on the outer surface of the catheter, microbial killing is achieved at the interface between the outer catheter surface and surrounding conductive medium such as tissue, blood, urine, skin, etc. Iontophoretic action is thereby achieved between electrodes 16 and 18 as current is being discharged across the positive and negative polarity electrode pairs. It is important to note that, like the embodiment illustrated in FIG. 3A, electrode pairs 16 and 18 can be placed on the outer surface of any medical tool including, but not limited to a catheter. The medical tool may be a bone stabilization pin 36, catheter 28, bandage 27 or various other applications such as artificial joints, artificial tracheas, intubation tubes, chest tubes, and drains. As shown in FIG. 3B, electrode pairs 16 and 18 can be placed within a wound dressing including, but not limited to, a bandage.

Figure 4C:
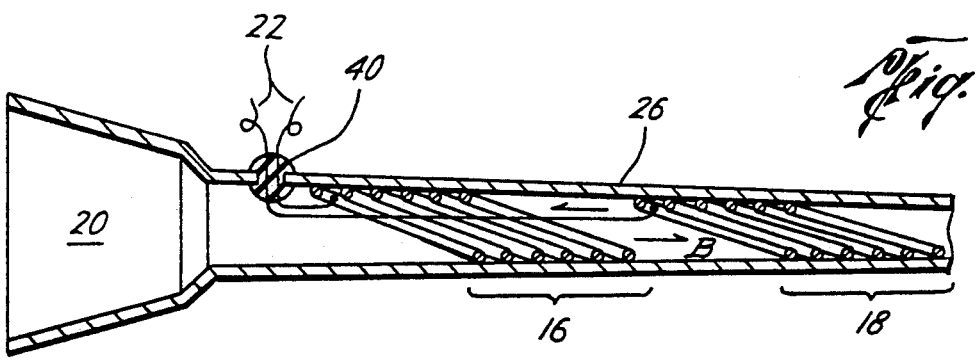

Referring to FIG. 4C, an alternative arrangement of electrodes 16 and 18 is shown. Electrode 16 is placed about a first portion of the inside of a catheter while electrode 18 is placed about a second portion of a catheter, wherein the first and second portions are axially spaced from each other. By separating a plurality of electrodes 16 from another plurality of electrodes 18, greater iontophoretic effect may be achieved by increasing the "net" current at each electrode site thereby correspondingly increasing the ionic flow between the electrode sites. As conductive medium 20 flows through electrodes 16 and 18 in accordance with reference flow numeral B, bacteria and yeast within the medium is continuously killed as it passes the electrode sites. The embodiment shown in FIG. 4C therefore can be advantageously used for killing microbes flowing at high volumetric rates possibly for use in control of biofilms.

Figure 4D:
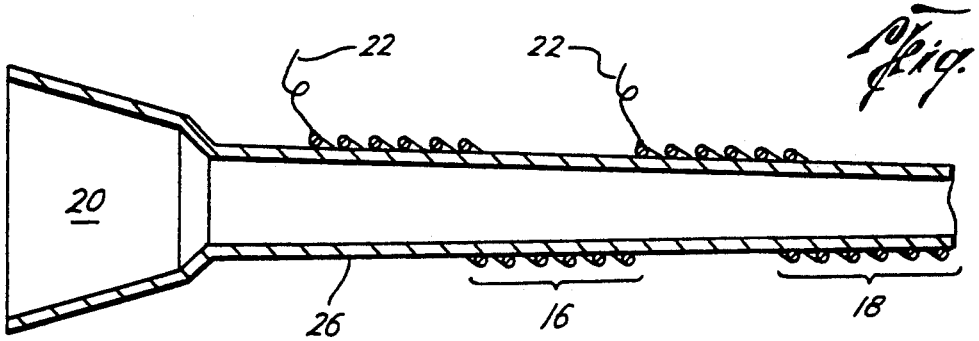

FIG. 4D illustrates that electrode sites, having electrodes 16 and 18, can be arranged on the outer surface of catheter 26 as well. Thus, sterilization is achieved at the interface between the catheter and surrounding conductive medium.

Figure 5:
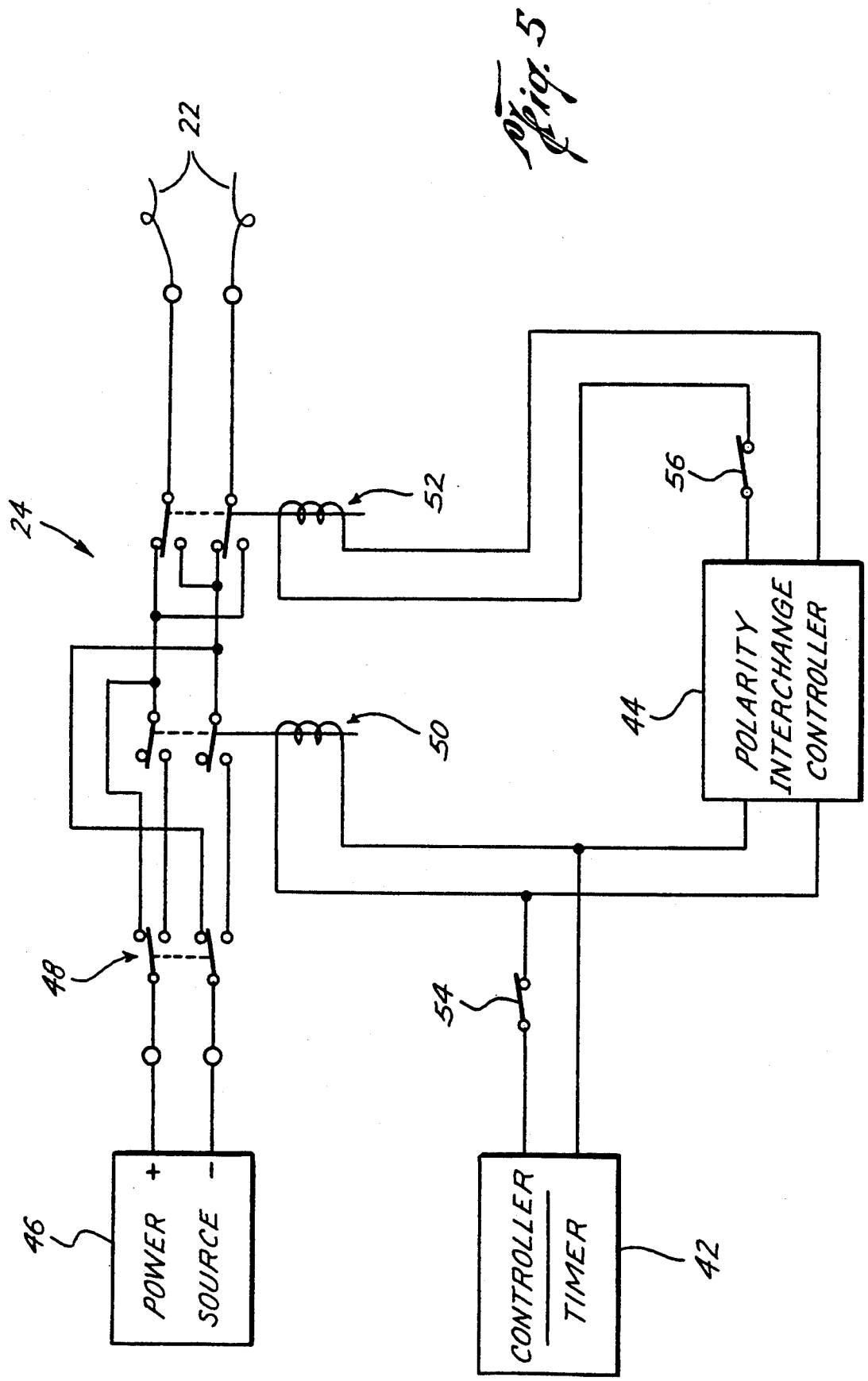
FIG. 5 is a block circuit diagram of an intermittent current source with polarity interchange in accordance with the present invention.

Turning now to FIG. 5, current source 24 is illustrated comprising an intermittent controller timer 42 and polarity interchange controller 44. Current source 24 is fed by a low-power source 46 capable of generating from 20 to 400 microamps and at least 20 microamps over a period of 4 hours in order to kill various forms of microbes, of which a small sample is described below. Switch 48 is used to bypass intermittent controller/timer 42. When placed in the position shown in FIG. 5, switch 48 allows direct application of voltage from power source 46 to the input of relay 50 actuated by polarity interchange controller 44. Thus, the position of switch 48 determines whether or not intermittent controller/timer 42 is activated or deactivated. If the poles of switch 48 are moved downward such that voltages are applied to the input poles of relay 50, then activation of relay 50 via switch 54 will cause intermittent voltage at the input of relay 52 actuated by polarity interchange controller 44. Intermittent voltage introduced through wires 22 can have a varying periodicity necessary to prevent early precipitation formation and early electrode deterioration. Preferably, intermittent voltage periodicity ranges between a fraction of a second to several seconds.

Polarity interchange controller 44 functions simultaneous with intermittent controller/timer 42 provided switch 56 is activated thereby inducing relay 52 and reversing the polarity on output wires 22. Each polarity interchange occurs over a period of time not to exceed the lifespan of the electrodes. Thus, polarity interchange periodicity may be several weeks but to maintain even precipitation rejection, periodicity preferably ranges between a minute to several minutes. As indicated above, power source 46 can operate off either conventional 120 volt power source or a six-volt battery. A voltage regulator may be used within source 46 to produce output current into a high impedance load, if necessary. In most human applications voltage requirements can vary between 2–3.5 volts to produce 400 $\mu A$.

Figure 12:
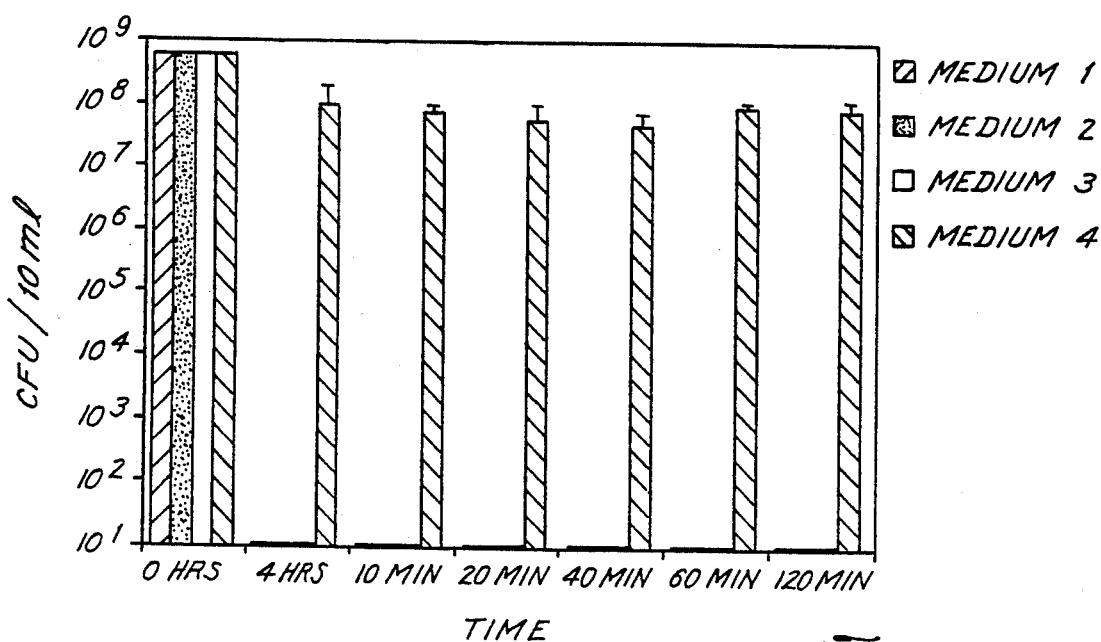
FIG. 12 is a graph showing actual results of iontophoresis killing in four different media in accordance with the present invention.
Figure 13:
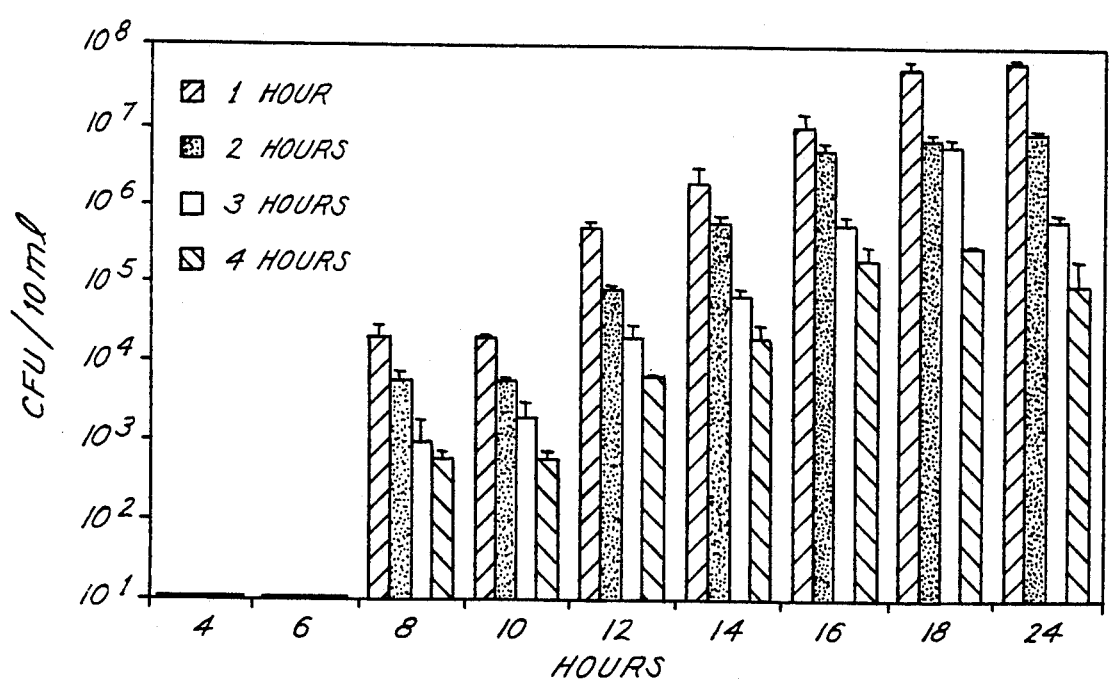
FIG. 13 is a graph showing actual results of residual killing of Escherichia coli from 4 hours to 24 hours after initial sterilization in accordance with the present invention.

Referring now to FIGS. 6–14, actual results of iontophoresis of the present invention are charted for killing various forms of microbes. FIGS. 6–11 illustrate iontophoretic killing in media containing various forms of microbes using electrodes comprising gold (Au), carbon (C) or platinum (Pt). FIG. 12 illustrates iontophoresis of the present invention within four different media, and FIGS. 13 and 14 illustrate the residual killing effect of iontophoresis upon microbes, including bacteria or yeast-like fungus, according to the present invention. It is important to note that the present invention is certainly not limited to killing the microbia species described in FIGS. 6–14. Instead, the present invention is contemplated as being able to kill any form of microbes found within or on a conductive medium.

Figure 6:
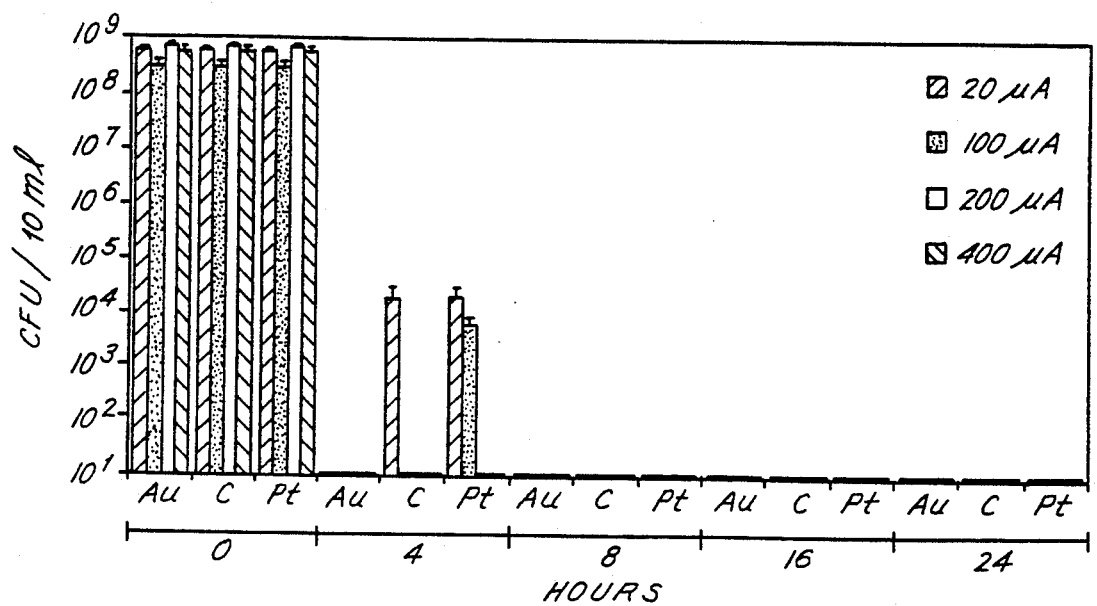
FIG. 6 is a graph showing actual results of iontophoresis killing of Escherichia coli in accordance with the present invention.

Turning now to FIG. 6, actual results of iontophoresis in a medium containing bacteria called Escherichia coli using gold, carbon or platinum electrodes and using various current levels is shown. As indicated, higher current levels provide quicker sterilization or decline in the concentration of bacteria measured in CFU (colony-forming units) per 10 ml sample. The graph indicates that Escherichia coli can be essentially eliminated to less than 10 CFU per 10 ml in a relatively short period of time. It appears as though gold electrodes provide a more efficient killing source. However, non-metal electrode, e.g. carbon, also provides killing as described by the anti-microbial effect of the present invention.

Figure 7:
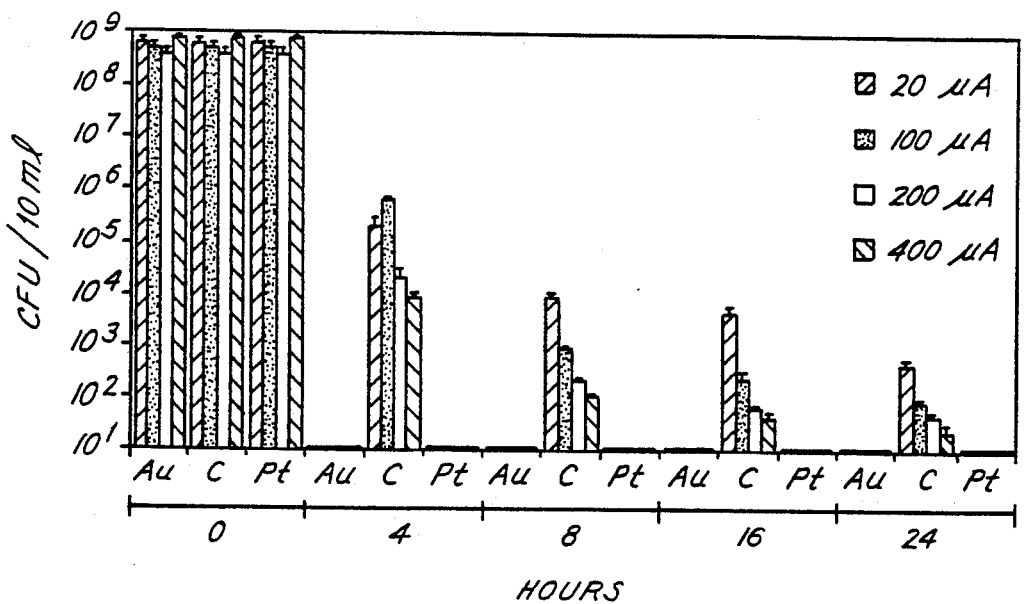
FIG. 7 is a graph showing actual results of iontophoresis killing of Proteus species in accordance with the present invention.
Figure 8:
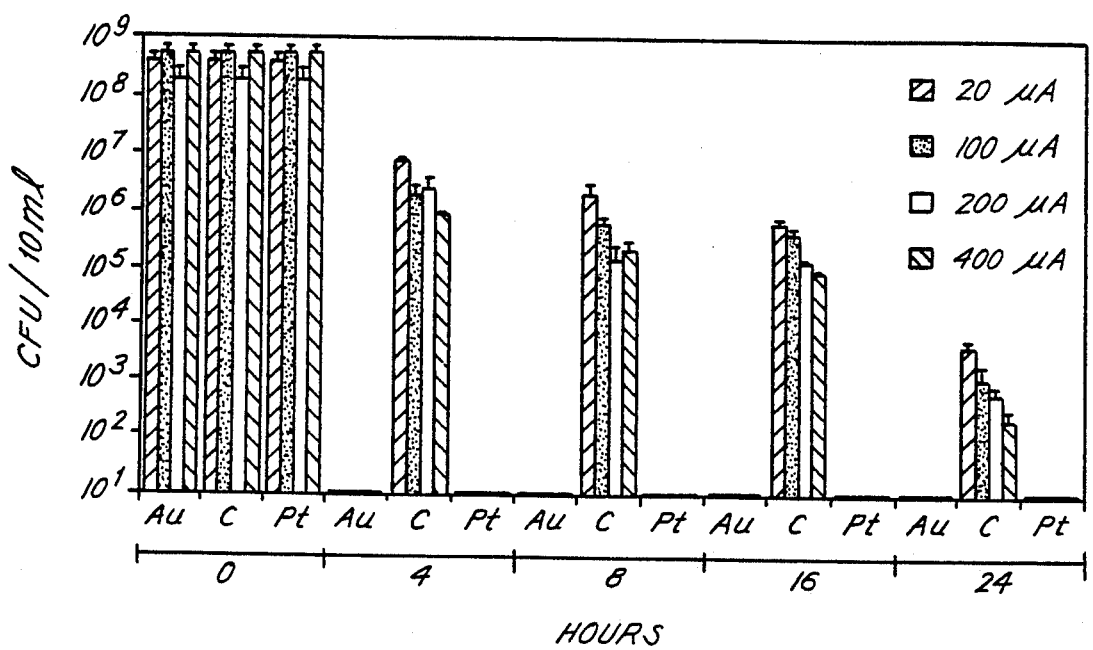
FIG. 8 is a graph showing actual results of iontophoresis killing of Klebsiella pneumoniae in accordance with the present invention.
Figure 9:
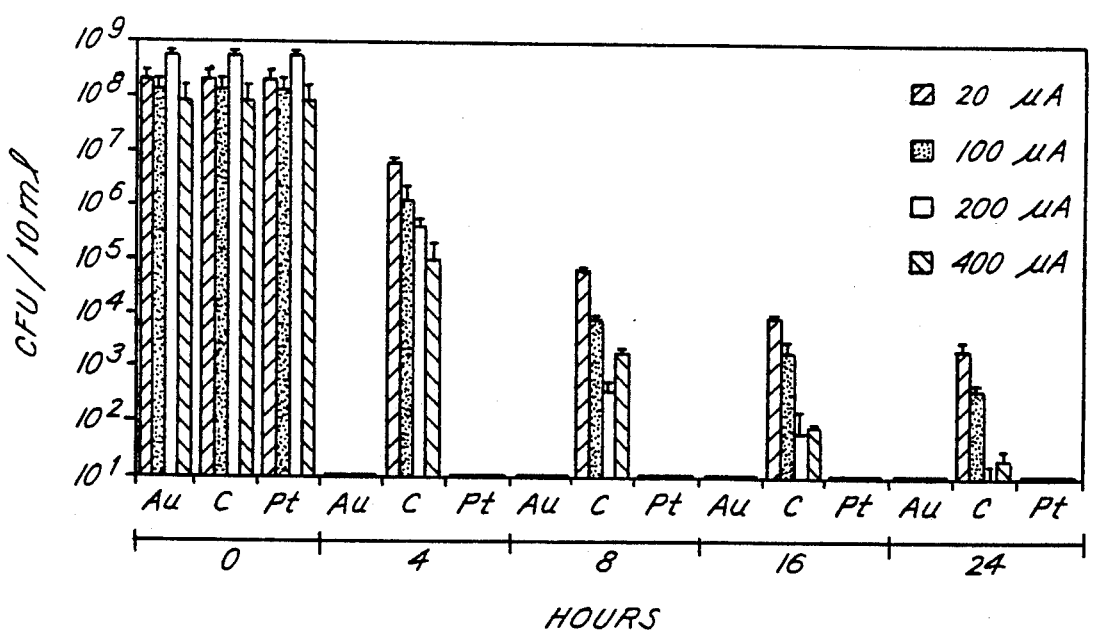
FIG. 9 is a graph showing actual results of iontophoresis killing of Pseudomonas aeruginosa in accordance with the present invention.
Figure 10:
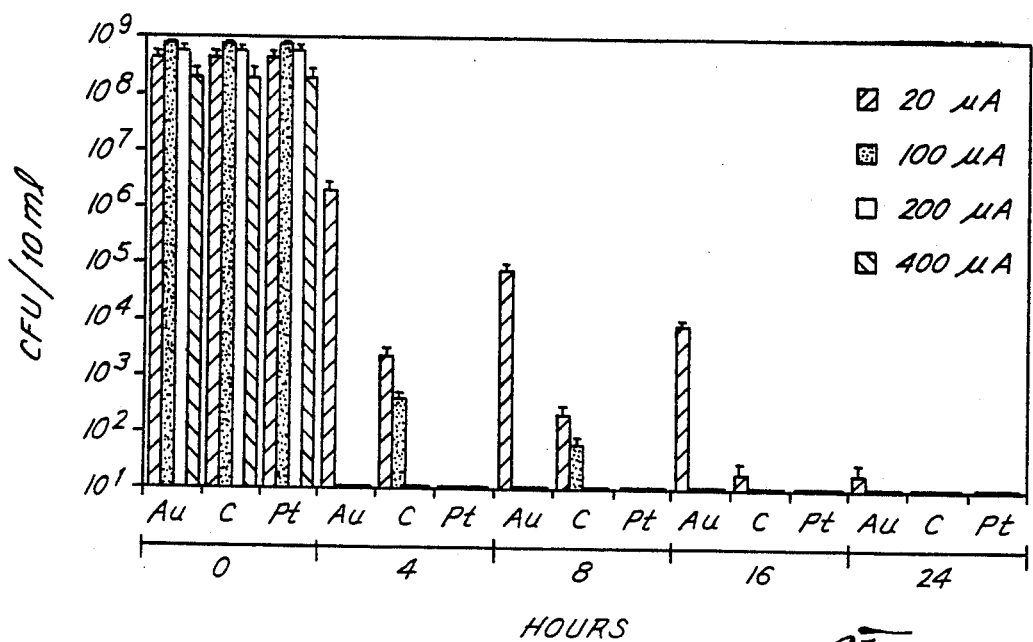
FIG. 10 is a graph showing actual results of iontophoresis killing of Staphylococcus species in accordance with the present invention.
Figure 11:
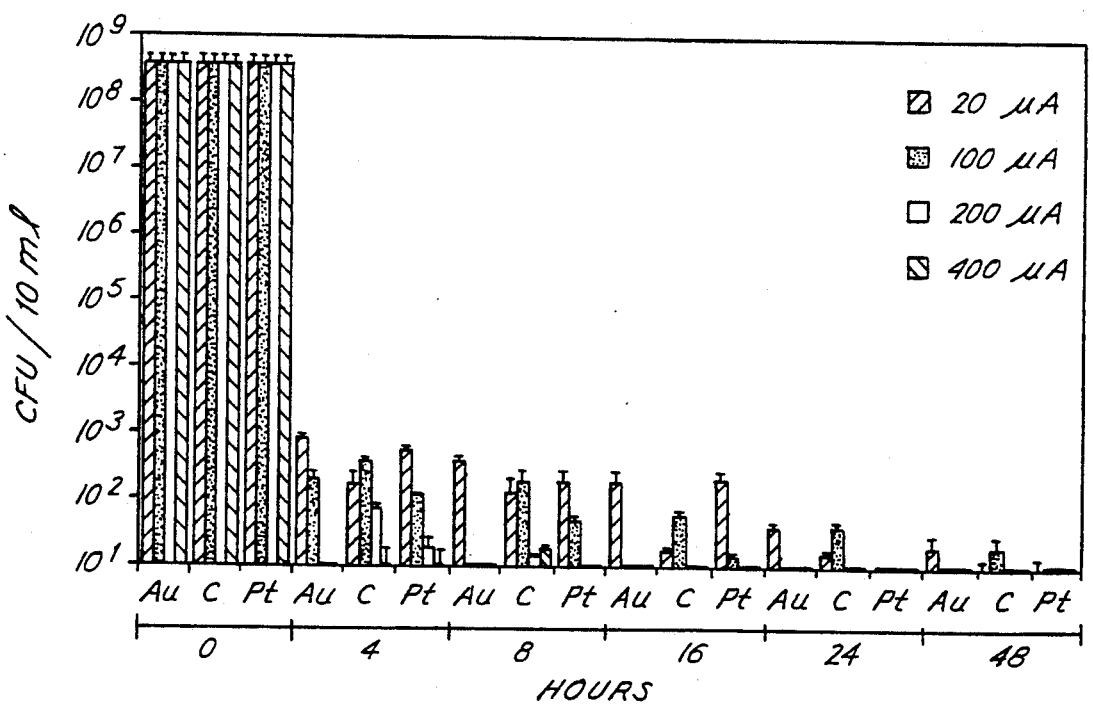
FIG. 11 is a graph showing actual results of iontophoresis killing of Candida albicans in accordance with the present invention.

FIG. 7 illustrates actual results of iontophoresis for Proteus species of bacteria at various treatment times, current levels and electrode compositions. Proteus species appear less susceptible to sterilization using carbon electrodes, but clearly indicates long-term carbon electrode sterilization. FIG. 8 illustrates actual results of iontophoresis for Klebsiella pneumoniae bacteria, and also indicates the lessened, yet effective killing achieved by carbon electrodes. FIG. 9 illustrates actual results of iontophoresis for Pseudomonas aeruginosa bacteria as another form of bacteria upon which iontophoresis of the present invention is effected. Still further, FIGS. 10 and 11 also indicate the relative effectiveness of carbon electrode (as opposed to metallic gold and platinum electrodes) of iontophoresis for Staphylococcus species and Candida albicans, respectively.

FIG. 12 illustrates the sterilization effect using iontophoresis of the present invention in four different media for comparison purposes. Medium 1 was prepared with 1 gram per liter of $KH_2PO_4$, 3 grams per liter $K_2HPO_4$, 5 grams per liter $NH_4Cl$, 1 gram per liter $NH_4NO_3$, 2 grams per liter $Na_2SO_4$, 0.0001 grams per liter $CaCl_2$ and 0.0001 grams per liter $MgSO_4$. Medium 2 is prepared with 1 gram per liter $KH_2PO_4$, 3 grams per liter $K_2HPO_4$, 5 grams per liter $NH_4Cl$, 1 gram per liter $NH_4NO_3$, and 2 grams per liter $Na_2SO_4$. Medium 3 is prepared with 5 grams per liter $NH_4Cl$, 1 gram per liter $NH_4NO_3$, and 2 grams per liter $Na_2SO_4$. Medium 4 is prepared with 1 gram per liter $KH_2PO_4$ and 3 grams per liter $K_2HPO_4$. FIG. 12 illustrates actual antimicrobial results on Candida albicans using gold electrodes at 400 microamps. Furthermore, FIG. 12 indicates effective and substantial killing of microbes in less than four hours for all of the media except for medium 4. An important dissimilarity between medium 4 and media 1, 2, and 3, as shown above, is that medium 4 does not include the element chlorine. Media 1, 2, and 3 in fact do include chlorine as an element within the inorganic salt $NH_4Cl$.

Thus, as indicated by FIG. 12, some effective antimicrobial agents are likely derived from inorganic salts contained within the conductive medium. Even if the electrodes are non-metallic, such as electrodes made of carbon, microbes can be killed in the presence of an antimicrobial agent such as chlorine. As FIG. 12 indicates, antimicrobial effect necessary for iontophoresis may in fact come from the chemical composition of the conductive medium and not solely from the electrode composition. The distinction is important not only for determining the killing source, but also lends evidence that residual killing may be present for a finite time within the medium after iontophoresis ceases. If the medium contains the antimicrobial agent as put forward by the present invention, then residual killing can occur without having to constantly drive the iontophoretic path. Killing may occur even after the source is discontinued provided antimicrobial agents are initially released via electrical stimulation. Thus, as contemplated by the present invention, current source 24 need not be a constant source but can be intermittent only for the period of time necessary to generate antimicrobial agents from components in the medium. As opposed to conventional iontophoresis wherein a constant current source is needed to drive antimicrobial heavy metal ions from the surface of the electrode, the present device maintains antimicrobial activity even after current is discontinued. Once the current is discontinued, "heavy metal" iontophoresis ceases and the residual effect, if any, is maintained via the antimicrobial agent contained within or on the medium.

As indicated in FIG. 13, residual killing appears to be occurring from within the conductive medium itself. Even after current from current source 24 ceases, some iontophoretic effect continues killing Escherichia coli for almost 8 hours. FIG. 13 indicates actual post-iontophoretic killing and subsequent bacteria growth from a period right after the electrode current is deactivated to approximately 24 hours thereafter. This is clearly shown if the iontophoretic current is turned off and then an inoculum of organisms is added. One hour later the original inoculum is subcultured (post-inoculum subculture) and the survivors counted. This is done repeatedly to determine the residual effect of the iontophoretically generated antimicrobial agent(s). The data shows sterilization up to 6 hours after iontophoresis ceases and shows clear population reduction proportional to the time in which the bacteria is exposed to post iontophoretically generated antimicrobial agents.

Similar to the residual killing effect for microbial contamination shown in FIG. 13, residual killing of yeast-like fungus Candida albicans can also be obtained, as illustrated in FIG. 14. Even after current from current source 24 ceases, some iontophoretic effect remains thereby maintaining the killing of yeast-like fungus for almost 8 hours.

Because of the post-iontophoretic antimicrobial generation contained within the medium, intermittent current may be used with equal effectiveness in sterilization procedures. As indicated in the following experimentally derived table, electrode life is significantly minimized when a constant current source is used:

TABLE 1

| ELECTRODE TYPE | MICRO AMPS (CONSTANT) | LIFESPAN |
|---|---|---|
| Gold (AU) | 200 | 12–13 days |
| Gold (AU) | 400 | 9–10 days |
| Platinum (PT) | 200 | 180 days |
| Platinum (PT) | 400 | 180 days* |

*Note:
180 days was the extent of the experiment. Platinum electrodes appear effective in killing CFU's and did not break off or cease operation after 180 days. Gold electrodes broke and thus breakage determined their lifespan.

In accordance with the present invention, intermittent controller/timer 42 in combination with polarity interchange controller 44 can extend either metallic or non-metallic electrode longevity beyond 180 days. By applying an intermittent current to the electrodes, residual iontophoretic killing within the medium is fully utilized without having need for a constant current source. Furthermore, by reversing or switching the polarity upon each electrode, the useful life of the electrodes is further extended by substantially preventing precipitation accumulation upon the electrodes. Thus, not only does intermittent/reverse polarity current source reduce out-migration but it also reduces the amount of accumulation upon the electrode. The length and duration of the intermittent current pulses is defined herein as any length necessary to maintain residual killing but which minimizes decay or effectiveness of the electrodes. Preferably, intermittent/reverse polarity current will be applied to extend the life of the electrodes beyond 180 days so that iontophoretic applications are practical in commercial large-scale operations.

The foregoing description of the present invention has been directed to several preferred embodiments. It will be apparent, however, to those skilled in the art that modifications and changes in both apparatus and method may be made without departing from the scope and spirit of the invention. For example, electrodes 16 and 18 can be placed in any conductive medium and can be configured as plates or wires housed in any form upon or within any fixture. Further, the arrangement of electrode sites can be varied in order to adapt to either large-scale or small-scale iontophoretic setting. Still further, intermittent controller 42 and polarity interchange controller 44 are operable to produce any wave shape or timed polarity interchange as long as the defined purpose is to maintain sterilization while prolonging electrode life. Even still further, microbial or bacterial species beyond those described in FIGS. 6–14 can be killed with substantially equal effectiveness in accordance with the present invention. In fact, FIG. 14 shows that yeast-like fungus Candida albicans, responds similar to the tested bacteria. Therefore, it is the intention of the present invention to set forth within the following claims all such equivalent modifications and variations which fall within the true spirit and scope of this invention.

What is claimed is:

1. An apparatus for killing microbes in a conductive medium, comprising:
   a positive and a negative electrode spaced apart from one another and placeable in a conductive medium, each postive and negative electrode being formed from an element including carbon;
   an intermittent current source connected to said positive and negative electrodes; and
   means for activating said source in periodic reverse polarity for generating antimicrobial agents from inorganic salts within said conductive medium.

2. The apparatus as recited in claim 1, wherein said positive and negative electrodes are spaced adjacent each other and are placed about the inside of a catheter.

3. The apparatus as recited in claim 1, wherein said activating means comprises an electrode polarity interchange circuit connected between said intermittent current source and said positive and negative electrodes.

4. The apparatus as recited in claim 3, wherein said electrode polarity interchange circuit comprises means for substantially reducing precipitation occurring between and upon said positive and negative electrodes.

5. A method for sterilizing a conductive medium, comprising:
   placing positive and negative electrodes apart from each other and into said conductive medium, each postive and negative electrode being formed from an element including carbon;
   connecting said positive and negative electrodes to an intermittent current source; and
   activating said current source in periodic reverse polarity, whereby antimicrobial agents are released from inorganic salts contained within said conductive medium.

6. The method as recited in claim 5, wherein said connecting step comprises:
   attaching said positive and negative electrodes to positive and negative poles, respectively, of said intermittent current source, for a first period of time; and
   subsequently attaching said positive and negative electrodes to negative and positive poles, respectively, of said current source for a second period of time to prolong the useful life of said positive and negative electrodes and prevent precipitation accumulation on and between said electrodes.

7. The method of claim 5 wherein said conductive medium is a biological fluid.

8. The method of claim 7 wherein said conductive medium comprises blood.

9. The method of claim 7 wherein said conductive medium comprises urine.

10. The method of claim 7 wherein said conductive medium comprises tissue fluid.

11. The method of claim 5 further comprising, confining said conductive medium in a vessel.

12. The method of claim 11 wherein the vessel is physiological.

13. The method of claim 12 wherein the vessel is an internal organ.

14. The method of claim 12 wherein the vessel is an artery.

15. The method of claim 12 wherein the vessel is a vein.

16. A method for sterilizing a chlorine containing conductive medium, comprising:
   placing positive and negative electrodes apart from each other and into said conductive medium, each positive and negative electrode being formed from an element including carbon;
   connecting said positive and negative electrodes to an intermittent current source; activating said current source in periodic reverse polarity; releasing antimicrobial agents within said conductive medium; and sterilizing said conductive medium by said antimicrobial agents.

17. The method as recited in claim 16, wherein said connecting step comprises:
   attaching said positive and negative electrodes to positive and negative poles, respectively, of said intermittent current source, for a first period of time; and
   subsequently attaching said positive and negative electrodes to negative and positive poles, respectively, of said current source for a second period of time to prolong the useful life of said positive and negative electrodes and prevent precipitation accumulation on and between said electrodes.

18. A method for sterilizing a conductive medium, comprising:
   providing a halide containing conductive medium;
   placing positive and negative electrodes apart from each other and into said conductive medium, each postive and negative electrode being formed from an element including carbon;
   connecting said positive and negative electrodes to an intermittent current source; and
   activating said current source in periodic reverse polarity;

releasing antimicrobial agents from said halide containing conductive medium; and sterilizing said conductive medium by said antimicrobial agents.

19. The apparatus as recited in claim 1, wherein said positive and negative electrodes are spaced adjacent each other and are placed about the outside of a catheter.

20. The apparatus as recited in claim 1, wherein said positive electrode is wound about a first portion of the inside of a catheter and said negative electrode is wound about a second portion of the outside of said catheter, wherein said first portion is axially spaced from said second portion.

21. The apparatus as recited in claim 1, wherein said positive electrode is wound about a first portion of the outside of a catheter and said negative electrode is wound about a second portion of the outside of said catheter, wherein said first portion is axially spaced form said second portion.

22. The method of claim 5, wherein said conductive medium comprises a gas.

23. The method of claim 5, wherein said conductive medium comprises fluid from a water treatment plant.

24. The method of claim 18, wherein said halide comprises bromine.

25. The method of claim 18, wherein said halide comprises fluorine.

26. The apparatus as recited in claim 1, wherein said positive and negative electrodes are spaced adjacent each other and are placed with a dressing.

* * * * *

UNITED STATES PATENT AND TRADEMARK OFFICE
CERTIFICATE OF CORRECTION

PATENT NO. : 5,328,451
DATED : July 12, 1994
INVENTOR(S) : Davis et al

It is certified that error appears in the above-indentified patent and that said Letters Patent is hereby corrected as shown below:

In claim 21, column 14, line 4, change "form" to --from--.

In claim 18, column 12, line 63, change "postive" to --positive--.

Signed and Sealed this

Eighteenth Day of October, 1994

Attest:

BRUCE LEHMAN

Attesting Officer

Commissioner of Patents and Trademarks